United States Patent [19]

Sonnenberg

[11] 4,024,119

[45] May 17, 1977

[54] POLYSULFONE RESINS CONTAINING BIBENZYL SULFONE REPEATING UNITS

[75] Inventor: Fred Max Sonnenberg, Worcester, Mass.

[73] Assignee: Foster Grant Co., Inc., Leominster, Mass.

[22] Filed: Jan. 12, 1976

[21] Appl. No.: 648,445

[52] U.S. Cl. .................. 260/79.3 A; 260/79.3 R; 260/543 H; 260/607 AR; 260/DIG. 23
[51] Int. Cl.$^2$ .................. C08F 28/02; C08G 75/20
[58] Field of Search ................ 260/79.3 A, 79.3 R, 260/607 AR, 543 H

[56] References Cited

UNITED STATES PATENTS

| 2,445,569 | 7/1948 | Fox ................................ 260/79.3 R |
| 3,629,170 | 12/1971 | Yamanouchi et al. ........ 260/79.3 R |
| 3,726,927 | 4/1973 | Leslie et al. .................. 260/79.3 A |
| 3,787,363 | 1/1974 | Staniland et al. ............. 260/79.3 R |
| 3,830,848 | 8/1974 | Siegrist ........................ 260/607 AR |
| 3,875,103 | 4/1975 | Leslie ............................... 260/79 |
| 3,956,395 | 5/1976 | Meyer .............................. 260/79 |

FOREIGN PATENTS OR APPLICATIONS

| 1,060,546 | 3/1967 | United Kingdom .......... 260/79.3 R |
| 1,122,192 | 7/1968 | United Kingdom .......... 260/79.3 R |
| 1,166,624 | 10/1969 | United Kingdom .......... 260/79.3 R |
| 1,337,434 | 11/1973 | United Kingdom .......... 260/79.3 R |

*Primary Examiner*—Ronald W. Griffin
*Attorney, Agent, or Firm*—Michael J. Tully

[57] ABSTRACT

Sulfone polymers are disclosed containing bibenzyl sulfone repeating units having the formula

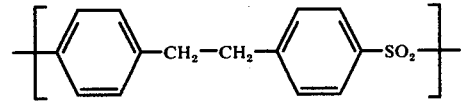

These polymers exhibit good mechanical properties, toughness, flexiblity, thermal and chemical stability and can be heat processed, extruded, drawn or otherwise formed into shaped articles having a high degree of strength and good dielectric properties.

18 Claims, No Drawings

POLYSULFONE RESINS CONTAINING BIBENZYL SULFONE REPEATING UNITS

BACKGROUND OF THE INVENTION

The present invention is concerned with thermoplastic poly bibenzyl sulfone polymers and copolymers containing recurring bibenzyl sulfone groups in the polymer molecule, said polymers and copolymers exhibiting high temperature stability and improved tensile properties as compared with conventional aromatic sulfone polymers.

There are a number of polymers available today which offer extremely good resistance to heat at temperatures in excess of 100° C, good electrical properties and are relatively inert to attack by chemical solvents. Among these materials are the polyphenylene oxides, polysulfones, polysulfonates, polysulfone polyesters, polysulfonamides and like materials. These polymers are generally characterized by recurring phenyl or biphenyl groups joined together by sulfur, oxygen, sulfone, amide or bivalent hydrocarbon radicals.

One commercially available polysulfone is produced by the reaction between the sodium salt of 2,2 bis (4-hydroxy phenol) propane and 4,4'-dichlorodiphenyl sulfone. This material is characterized as being stable in air at temperatures in excess of 300° F and is fairly rigid, exhibiting a flexural modulus of elasticity of nearly 400,000 psi at room temperature. Another class of polysulfone polymers are the polyaryl sulfones such as, for example, disclosed in British Patent specification No. 1,122,192. These polymers are amorphous and consist mainly of phenyl and biphenyl groups linked by thermally stable ether and sulfone groups, and may be distinguished from polysulfones mentioned above by the absence of aliphatic groups. The molding grade polyaryl sulfones may be processed by injection molding or extrusion techniques, but extremely high temperatures are required. For example, the cylinder and nozzle of an injection molding machine must normally be equipped to reach temperatures of 800° F., and temperatures in the range of about 600° F. to 750° F. are required for extrusion. Other polyaryl sulfones exhibiting similar properties are taught in British Patent specification No. 1,166,624 in which polymers having a diphenyl ether sulfone repeating unit in the polymer chain are prepared, and British Patent specification No. 1,060,546 in which sulfone copolymers containing diphenyl ether sulfone and at least one other aromatic sulfone such as biphenyl, diphenyl methane or naphthalene are prepared.

Whereas the above and other sulfone polymers have filled a long felt need for thermoplastic materials which do not degrade at temperatures in excess of 100° C. and in many cases at temperatures up to about 500° C., their thermal characteristics are such that extremely high temperatures are required to process them. This in turn may require the use of special or modified processing equipment adapted for high temperatures and the consumption of large amounts of energy.

Accordingly, it is an object of this invention to provide aromatic sulfone polymers which exhibit toughness, flexibility, high temperature stability, good tensile stress properties, a relatively high heat distortion temperature, and good dielectric properties.

Another object of this invention is to provide a novel monomer suitable for the preparation of sulfone polymers and copolymers.

Still another object is to provide aromatic sulfone homopolymers and copolymers containing bibenzyl sulfone units which exhibit superior tensile stress and processing properties.

SUMMARY OF THE INVENTION

This and other objects of the invention may be achieved by preparing polysulfone homopolymers having the repeating bibenzyl sulfone unit of the formula:

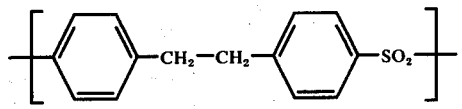

or copolymers having this unit chemically linked through the sulfone group of different aromatic units such as biphenyl, diphenyl ether, diphenyl sulfide and like aromatics. Polybibenzyl sulfone homopolymers may be most readily prepared by either forming the self condensation product of bibenzyl-4-sulfonyl chloride using a Lewis acid catalyst, or by reacting approximately stiochiometric molar amounts of bibenzyl and bibenzyl-4,4'-disulfonyl chloride also employing a Lewis acid catalyst. Copolymers may be prepared by the same method by copolymerizing the appropriate amounts of bibenzyl or its mono or di sulfonyl chloride derivative with the selected comonomer or comonomers or their mono or di sulfonyl chloride derivatives. Bibenzyl sulfone polymers prepared according to this invention exhibit good high temperature stability, tensile strength, and flexibility. Also, polymers containing a major amount of bibenzyl sulfone units may be processed using conventional molding or extrusion equipment. Shaped articles prepared from these polymers may be used in application where good high temperature stability and flexibility are prerequisites such as heat generating appliance housings or parts, circuit components, automotive parts, medical appliances, and the like.

DETAILED DESCRIPTION OF THE INVENTION

The polysulfones disclosed herein employ bibenzyl (diphenylethane) as the basic recurring structural moiety in the polymer backbone. Bibenzyl is a white crystalline compound which is insoluble in water and may be synthesized by treating benzyl chloride with metallic sodium or by the action of benzyl chloride on benzylmagnesium chloride. It may also be prepared by hydrogenating stilbene which, in turn, is manufactured as a by-product in the dehydrogenation of ethyl benzene during the manufacture of styrene. Stilbene may also be synthesized by passing toluene over hot lead oxide.

Polybibenzyl sulfone homopolymers are prepared by heating bibenzyl-4-sulfonyl chloride in the presence of a catalytic amount of an anhydrous Lewis acid, or by using a stoichiometric mixture of bibenzyl and bibenzyl-4,4'-disulfonyl chloride is hereinafter described. The preparation of the homopolymer first necessitates the synthesis of either the mono or di sulfonyl chloride derivative of bibenzyl. Bibenzyl-4-sulfonyl chloride may be prepared by a three step procedure by treating bibenzyl in solution with approximately equi molar quantities of chlorosulfonic acid to form bibenzyl-4-sulfonic acid followed by neutralization in an aqueous medium using sodium or barium hydroxide to yield the sodium or barium salt which is in turn treated in a solvent with an acid halide such as thionyl chloride to yield bibenzyl-4-sulfonyl chloride. Another suitable technique for the preparation of the monosulfonyl chloride derivative involves the treatment of the free sulfonic acid derivative of bibenzyl in a solvent with a complex of phosgene and a tertiary organic amide.

Bibenzyl 4,4'-disulfonyl chloride may be prepared by a three step procedure by sulfonation of bibenzyl using a molar excess of sulfuric acid to form bibenzyl 4,4-disulfonic acid, followed by neutralization and treatment with thionyl chloride as discussed above. It may also be prepared directly from bibenzyl by chlorosulfonation in chloroform using at least a two molar excess of chlorosulfonic acid. It has also been reportedly prepared by treatment of the sodium salt of bibenzyl disulfonic acid with phosphorous pentachloride and phosphorous oxychloride — Polymer Science, U.S.S.R., A-14, No. 9, 2102–2105, 1972.

The following Examples illustrate the preparation of bibenzyl-4-sulfonyl chloride and bibenzyl 4,4'-disulfonyl chloride respectively.

EXAMPLE I

To a solution of 54.6 g. (0.30 mole) of bibenzyl in 100 ml. of chloroform was added dropwise 24 ml. (0.372 mole) of chlorosulfonic acid in 40 ml. of chloroform. After stirring for two hours, the mixture was concentrated on a rotary evaporator and the solids washed with 100 ml. of hexane. There was obtained 78.7 g. of bibenzyl 4-sulfonic acid.

The above product was dissolved in 1600 ml. of water and filtered, yielding 71.1 g. of soluble product. This filtrate was further diluted with 800 ml. of water and treated with barium hydroxide until the solution was basic. The solids were filtered and dried resulting in a 78.1% yield of the barium salt of bibenzyl 4-sulfonic acid.

To 66.0 g. (0.10 mole) of the above salt in 500 ml. of DMF at 10° C was added dropwise 44 ml. (0.60 mole) of thionyl chloride. After one hour the mixture was gradually warmed to room temperature while stirring. The mixture was then mixed with 1 kg. of ice water and stirred for fifteen minutes. The solids were filtered, water washed and dried under vacuum yielding 52.1 g. of bibenzyl 4-sulfonyl chloride, mp. 83°–86° C.

The above solids were purified by refluxing in ligroin at a concentration of 5% by weight and by filtering out the resultant insolubles. The filtrate was concentrated and dried, yielding greater than 80% yield of purified bibenzyl 4-sulfonyl chloride, mp. 90° to 95° C.

Analysis: calculated: C, 59.8; H, 4.6; Cl, 12.6; S, 11.5. Found: C, 60.0; H, 4.8; Cl, 12.5; S, 11.4.

EXAMPLE II

To a solution of 36.4 g. (0.20 mole) of bibenzyl in 400 ml. of chloroform at 0° C. was added dropwise a solution of 105 ml. (1.60 mole) of chlorosulfonic acid in 100 ml. of chloroform. The cooling medium was removed and after one hour of stirring, the mixture was poured into 1 kg. of ice. The mixture was filtered and dried, yielding 50.7 g. of bibenzyl 4,4'-disulfonyl chloride, mp. 166°–185° C.

A 10 g. sample in a soxhlet tube was extracted overnight with 200 ml. of methanol. There was recovered after drying 7.8 g. of white solids, mp. 199°–205° C.

Analysis: calculated: C, 44.3; H, 3.2; Cl, 18.7; S, 16.9. Found: C, 43.6; H, 3.4; Cl, 18.2; S, 16.7.

As previously suggested, bibenzyl sulfone homopolymers and copolymers of the present invention may be effectively prepared by melt or solution polymerization technique. Polybibenzyl sulfone may be prepared using the self condensable bibenzyl 4-sulfonyl chloride monomer such as prepared in Example I, or by condensing equi molar quantities of bibenzyl and bibenzyl 4,4'-disulfonyl chloride such as prepared in Example II. Copolymers containing the bibenzyl moiety and one or more other aromatic moieties such as diphenyl ether, naphthalene, diphenyl sulfide and like aromatics may be prepared by copolymerizing an appropriate mixture of bibenzyl mono sulfonyl chloride with at least one other aromatic monosulfonyl chloride, or by copolymerizing a mixture comprising an aromatic disulfonyl chloride and unsubstituted aromatic.

The above monomers or comonomers may be substituted with non-reactive substituent groups on the aromatic nuclei. Such substituent groups include alkyl or perfluoroalkyl groups containing from about 1 – 5 carbon atoms, halogens such as bromine or chlorine and other substituents which are inert under the conditions of polymerization.

The polymerization process may be carried out using melt or solution condensation procedures involving a repeating reaction between an aromatic sulfonylchloride group and an aromatic hydrogen atom by heating the monomers to a temperature of about 80° to 250° C in the presence of a Friedel Crafts catalyst.

Suitable Friedel Crafts catalysts include metal salts or oxides such as ferric chloride, ferric bromide, ferric oxide, aluminum chloride, zinc chloride and antimony chloride. Anhydrous hydrofluoric acid or trifluoromethane sulfonic acid may also be used. These catalysts are generally effective in an amount of from 0.05 to 0.5 mole percent based on monomer amount.

Suitable inert solvents useful for solution polymerization include nitrobenzene and halogen containing aromatic or aliphatic solvents such as tetrachloro ethane, methylene chloride, chlorinated biphenyl and diphenyl ether, and like materials.

The general procedures for polymerization involves first heating the monomers or a solution of monomers to a temperature above the melting point to obtain a uniform melt. Then, an appropriate quantity of catalyst is added and the mixture is maintained at a polymerization temperature usually within the range of about 100° to 250° C for about 1 to 20 hours until polymerization is complete. The polymer may then be recovered by conventional techniques.

Polymers prepared according to the present invention will in general have an inherent viscosity in the range of about 0.2 to about 1.0 when determined as a 1% solution at 25° C in N-methyl-2-pyrrolidinone and may comprise the so-called AB type of polymers prepared by condensation reaction of bibenzyl monosulfonyl chloride or a mixture of bibenzyl monosulfonyl chloride with one or more different aromatic monosulfonyl chlorides, as represented by the following formulae:

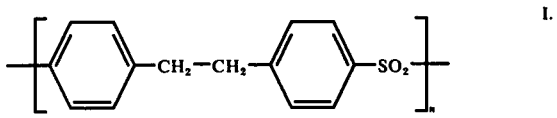

I.

wherein n is a positive whole number equaling the degree of polymerization and is such that the inherent viscocity of the polymer is within the range of about 0.2 to about 1.0 when determined as a 1% solution at 25° C in N-methyl-2-pyrrolidinone.

fone ($Z^1$ is oxygen), said terpolymers also containing at least 1 mole percent of bibenzyl sulfone units (formula III). It should be evident that suitable copolymers containing more than three different aromatic sulfone units would also be within the scope of this invention.

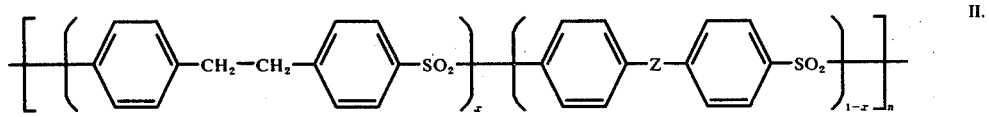

wherein $0.01 \leq x \leq 0.99$, and x equals the molar ratio of bibenzyl 4-sulfone units present in the total polymer weight, n is as defined above, and Z is selected from the group consisting of a direct link, oxygen, sulfur, lower alkylidene, or lower alkyl other than ethylene having from about 1 to 5 carbon atoms.

It is also possible to prepare so called AABB type polymers by the condensation reaction of approximately stoichiometric quantities of one of the 4,4'-disulfonyl chloride derivatives of any of the above recited monomers with one or more unsubstituted monomers. For example, polybibenzyl sulfone having repeating units as shown in formula I, can be prepared by reacting approximately equi molar amounts of bibenzyl

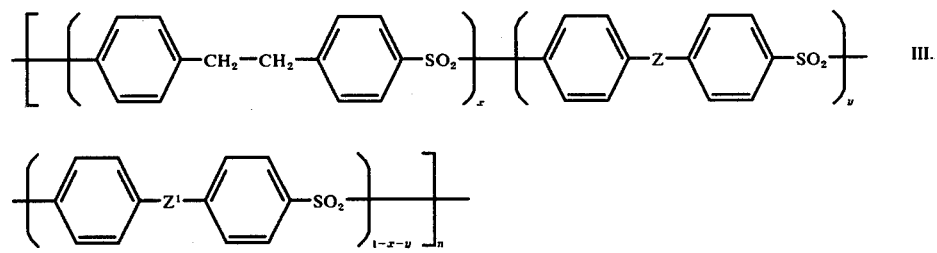

wherein: $0.01 \leq x < x + y \leq 0.99$, and x, Z and n are as defined above, y equals the molar ratio of $$\left( \bigcirc - Z - \bigcirc - SO_2 \right)$$

and bibenzyl 4,4¹-disulfonyl chloride. Copolymers may be prepared by reacting approximately equi molar quantities of an unsubstituted monomer containing aromatic groups and the 4,4¹-disulfonyl chloride derivative of another different monomer containing aromatic groups which copolymers may be represented by the formula:

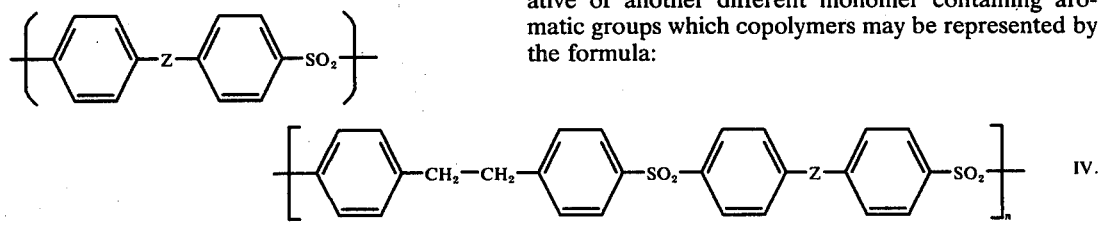

wherein Z and n are as defined above.

In a similar manner, terpolymers may be prepared by reacting approximately equi molar quantities of a 4,4¹-disulfonyl chloride monomer derivative and a mixture of unsubstituted monomers, or a mixture of different 4,4¹-disulfonyl chloride monomer derivatives with an approximately equi molar amount of an unsubstituted monomer. The structure of such polymers would be similar to that of formula III with the proviso that the polymer must contain about 50 mole percent of units derived from 4,4¹-disulfonyl chloride monomer or monomer mixture as represented by the following formula:

units present in the total polymer weight, and $Z^1$ is a member of Z different than the specific Z group present in the polymer.

Typical AB polymers corresponding to the above formulas include polybibenzyl sulfone (formula I); copolymers of bibenzyl sulfone copolymerized with biphenyl sulfone (Z is a direct link) or diphenyl ether sulfone (Z is oxygen), said copolymers containing at least 1 mole percent of bibenzyl sulfone units (formula II); and terpolymers of bibenzyl sulfone copolymerized with two different aromatic sulfone units such as biphenyl sulfone (Z is a direct link) and diphenyl ether sul-

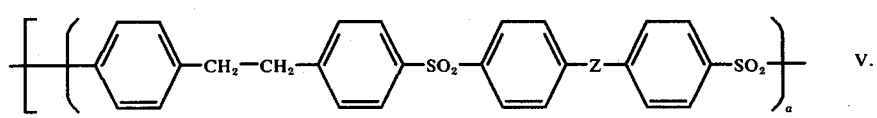

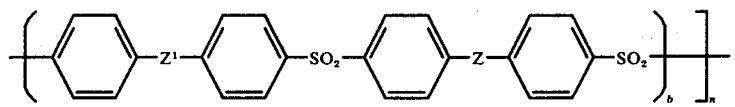

wherein $a$ and $b$ are positive whole numbers equal to 1 or greater but not neccessarily equal to each other, and $n$, $Z$ and $Z'$ are as defined above.

A typical polymer species represented by formula V would be the stoichiometric reaction product of diphenyl ether 4,4'-disulfonyl chloride ($Z$ is oxygen) with an approximately equi molar amount of bibenzyl and biphenyl ($Z'$ is a direct link).

The advantages of polymers prepared according to the present invention in terms of their low temperature processability are best realized in the polybibenzyl sulfone homopolymers or in copolymers containing at least about 25 mole percent of the bibenzyl sulfone moiety, more preferably in the order of at least about 50 mole percent. Such polymers generally exhibit melting point ranges in the order of 200° to 260° C as opposed to higher melting point ranges possessed by certain of the commercially available polysulfones.

The following Examples illustrate the preparation of the bibenzyl sulfone homopolymers and copolymers in accordance with the present invention.

EXAMPLE III

Solution homopolymerization of bibenzyl 4-sulfonyl chloride.

To a flamed out flask under nitrogen was added 5.6 g. (0.020 mole) of bibenzyl 4-sulfonyl chloride in 10 ml. of nitrobenzene. The mixture was warmed to 80° C. and 2.0 ml. of a 10% catalyst solution of ferric chloride in nitrobenzene was added. After a few minutes copious amounts of hydrochloric acid were liberated. The off gas was passed through water and then neutralized with 1N sodium hydroxide. After heating overnight at 120° C. a total of 39 ml. of base was needed to neutralize the off gases or 97.5% of the theoretical amount of HCl was liberated during the condensation polymerization. A total of 80 ml. of dimethyl formamide (DMF) was added and the solution heated for 10 minutes at 100° C. After filtration the mixture was slowly added to 500 ml. of methanol in a blender. The polymer was filtered and over dried. There was obtained 4.5 g. (91.4% yield) of polybibenzylsulfone, mp. 203°–205° C. The infrared spectra showed intense bands at 1300 and 1150 cm$^{-1}$ characteristic of sulfone absorption. The inherent viscosity as determined at 25° C as a 1% solution in N-methyl pyrrolidinone was 0.16.

EXAMPLE IV

Melt homopolymerization of bibenzyl 4-sulfonyl chloride.

To a flamed out polymer tube flushed with nitrogen was added 5.6 g. (0.02 mole) of bibenzyl 4-sulfonyl chloride. The tube was heated to 120° C in a tube furnace and then 0.1 g. of anhydrous ferric chloride was added. After one minute hydrochloric acid was liberated. The tube was heated to 250° C for two hours and attached to a vacuum pump for one hour.

To the cooled tube was added 50 ml. of DMF and ½ ml. of 2,4-pentanedione. The contents were heated for ten minutes at 100° C and some particles were filtered. The filtrate was added dropwise to 500 ml. of methanol in a blender. The polymer was washed with methanol and then dried in the oven. There was obtained 4.4 g., 89.5% yield of gray solids of polybibenzyl sulfone, mp. 200° – 210° C. The infrared spectra showed intense bands at 1300 and 1150$^{cm-1}$ characteristic of sulfone groups. The inherent viscosity as determined at 25° C. as a 1% solution in N-methyl pyrrolidinone was 0.22.

EXAMPLE V

This Example illustrates the preparation of polybibenzyl sulfone diphenylether sulfone copolymer containing approximately equi molar amounts of diphenyl ether and bibenzyl moieties. Under nitrogen was added 14.56 g. (0.08 mole) of bibenzyl, 29.96 g. (0.0816 mole) of diphenyl ether 4,4'-disulfonyl chloride and 30 ml. of nitrobenzene. The mixture was warmed to 120° C. and 0.20 g. of ferric chloride was added. After twelve hours at 120° C, the polymerization was terminated by the addition of 50 ml. of DMF, 1 ml. of aniline and ½ ml. of 2,4-pentanedione. The warm solution was added dropwise to 500 ml. of methanol in a blender. The polymer was filtered and extracted overnight with methanol and dried in an oven. There was obtained 27.4 g., 71.9% yield of polymer, mp. range 220° – 250° C.

EXAMPLE VI

This Example illustrates the preparation of polybibenzyl sulfone diphenyl sulfone copolymer containing approximately equi molar amounts of diphenyl and bibenzyl moieties. Under nitrogen was added 5.61 g. (0.02 mole) of bibenzyl 4-sulfonyl chloride, 5.06 g. (0.02 mole) of biphenyl 4-sulfonyl chloride and 40 ml. of nitrobenzene. The mixture was warmed to 120° C and then 0.10 g. of ferric chloride was added. After stirring overnight at 120° C, 50 ml. of dimethyl formamide, 1 ml. of aniline and 0.5 ml. of 2,4-pentanedione was added to the polymerization reaction. The hot mixture was added slowly to 500 ml. of methanol in a blender. The filtered polymer was washed numerous times with methanol and oven dried at 50° C. There was obtained 9.1 g., 98.7% yield of polymer having a melting point range of 270° – 293° C. and an inherent viscosity of 0.22 as determined as a 1% solution in N-methyl-2-pyrrolidinone.

EXAMPLE VII

A copolymer comprising polybibenzyl sulfone, diphenyl ether sulfone, copolybiphenyl diphenyl ether sulfone units was prepared according to the method of Example V using as monomers 29.96 g. (0.0808 mole) of diphenyl ether 4,4'-disulfonyl chloride, 3.65 g. (0.02 mole) of bibenzyl, 9.25 g. (0.06 mole) of biphenyl, and 30 ml. of nitrobenzene. At 110° C, 0.20 g. of ferric chloride catalyst was added and the mixture heated overnight at 120° C. There was obtained 34.7 g., 94.8% yield of dried polymer, mp. range of 280° – 290° C.

EXAMPLE VIII

A copolymer of polybibenzyl sulfone, diphenyl ether sulfone copolybiphenyl diphenyl ether sulfone was prepared according to the method of Example V using as monomers 14.68 g. (0.04 mole) of diphenyl ether 4,4'-disulfonyl chloride, 3.64 g. (0.02 mole) of bibenzyl, 3.08 g. (0.02 mole) of biphenyl, and 20 ml. of nitrobenzene and 4 ml. of ferric chloride catalyst solution.

There was obtained 16.8 g., 90.0% yield, of dried polymer mp. range of 255° – 260° C., vicat softening point of greater than 175° C. and inherent viscosity of 0.17.

Tensile and elongation properties of the polymers prepared in accordance with Examples V and VII, which exhibited good film forming properties, were evaluated by preparing films of these polymers in accordance with the following procedure:

To a 5.0 g. sample of polymer in a flask was added 12.5 ml of N-methyl-2-pyrrolidinone. The mixture was placed on a shaker overnight or longer to give a 40% solution.

Part of the 40% solution was placed on a photographic plate and the viscous material was drawn across the plate using a Gardner Film Casting Knife having an adjustable clearance controlled by micrometrics which was set for approximately 0.10 inches.

The plate with the cast film was dried overnight at 70° C in an air circulating oven. The film was either peeled off manually or chilled with dry ice to help remove it from the glass surface.

Films were also prepared under identical conditions with three samples of commercially available sulfone polymers designated as follows:

A — Copolymer of diphenyl ether sulfone and diphenyl sulfone (Imperial Chemical Ind. 720 P) having the structure:

B — Polyethersulfone (Imperial Chemical Ind. 200 P) having the structure:

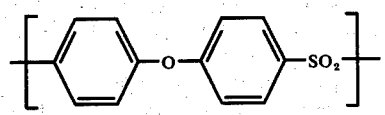

C — Polysulfone (Union Carbide — Udel 1700) having the structure:

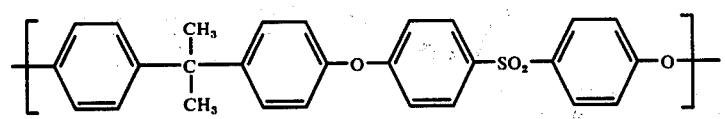

Comparative properties of these materials are recited in Table 1.

TABLE 1

| Polysulfone | M.P. Range ° C | Inherent Viscosity (NMP*) | Tensile Stress fail psi** | Percent elongation fail psi** |
|---|---|---|---|---|
| Example V | 229–250 | 0.54 | 5985 | 2.17 |
| Example VII | 280–290 | 0.54 | 5328 | 2.03 |
| A | 258–293 | 0.43 | 4676 | 2.90 |
| B | 235–273 | 0.51 | 3989 | 4.63 |

TABLE 1-continued

| Polysulfone | M.P. Range ° C | Inherent Viscosity (NMP*) | Tensile Stress fail psi** | Percent elongation fail psi** |
|---|---|---|---|---|
| C | 213–239 | 0.57 | 5095 | 2.27 |

*Determined as a 1% solution at 25° C in N-methyl-2-pyrrolidinone
**ASTM Test - D-882-73

Thermoplastic polymers prepared in accordance with the present invention may be characterized by a high degree of thermal and chemical stability and are ideally suited for use in the fabrication of shaped articles such as by molding or extrusion. They may also be processed into fibers or films or used as a component in adhesive compositions. Compositions based on the present polymers may also contain ingredients as are known in the polymer art such as pigments, fillers, lubricants, nucleating agents, stabilizers, plasticizers and like additives.

Although the invention has been described with particular reference to specific example, it should be understood that the invention should not be so limited but limited only by the scope of the appended claims.

What I claim is:
1. A homopolymer of bibenzyl sulfone.
2. A copolymer containing the following structural units:

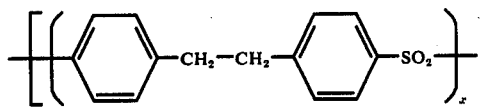

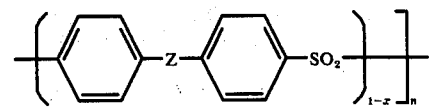

wherein: $0.01 \leq x \leq 0.99$; and
  $x$ equals the molar ratio of bibenzyl 4-sulfone units present in the total polymer weight;
  $n$ equals the degree of polymerization; and
  Z is selected from the group consisting of a direct link, oxygen, sulfur, lower alkylidene, or lower alkyl other than ethylene having from about 1 to 5 carbon atoms.
3. The copolymer of claim 2 wherein Z is oxygen.
4. The copolymer of claim 2 wherein Z is a direct link.
5. The copolymer of claim 2 having an inherent viscosity within the range of about 0.2 to 1.0 when measured at 25° C as a 1% polymer solution in N-methyl-pyrrolidinone.

6. The copolymer of claim 2 wherein $x$ ranges from about 0.25 to 0.50.

7. A terpolymer containing the following structural units:

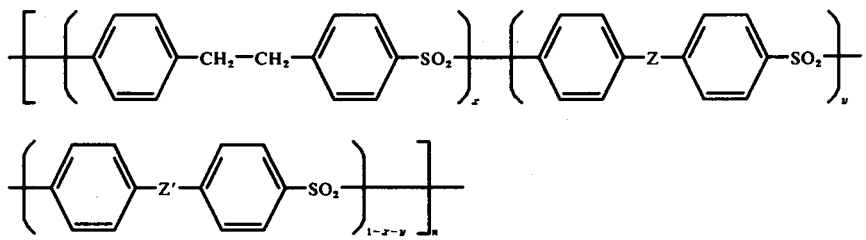

wherein: $0.01 \leq x < x + y \leq 0.99$; and

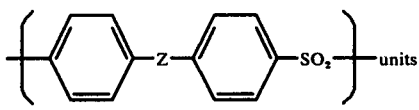

present in the total polymer weight;
$n$ equals the degree of polymerization;
Z is selected from the group consisting of a direct link, oxygen, sulfur, lower alkylidene or lower alkyl other than ethylene having from about 1 to 5 carbon atoms; and
Z' is a member of Z different than the specific Z group present in the polymer.

8. The copolymer of claim 7 wherein Z is a direct link and Z' is oxygen.

9. The copolymer of claim 7 having an inherent viscosity within the range of about 0.2 to 1.0 when measured at 25° C as a 1% polymer solution in N-methyl-2-pyrrolidinone.

10. The copolymer of claim 7 wherein $x$ ranges from about 0.25 to 0.50.

11. A copolymer having the structure:

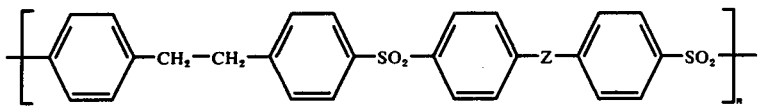

$n$ equals the degree of polymerization and is such that the inherent viscosity of the copolymer is within the range of about 0.2 to 1.0 when determined as a 1% solution at 25° C in N-methyl-2-pyrrolidinone;
Z is selected from the group consisting of a direct link, oxygen, sulfur, lower alkylidene, or lower alkyl other than ethylene, having from about 1 to 5 carbon atoms.

12. The copolymer of claim 11 wherein Z is oxygen.

13. A polymer product containing the following structural units:

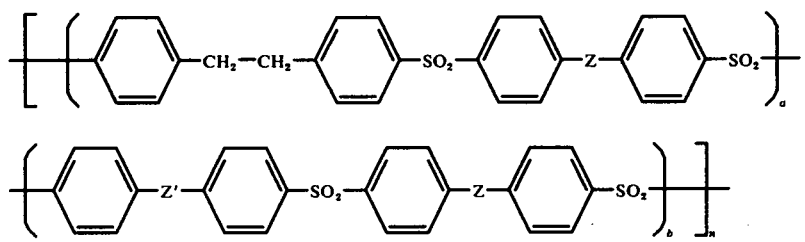

wherein:
Z is selected from the group consisting of a direct link, oxygen, sulfur, lower alkylidene or lower alkyl other than ethylene having from about 1 to 5 carbon atoms;
Z' is a member of Z different than the specific Z group present in the polymers;
$a$ and $b$ are positive whole numbers equal to or greater than 1 but not necessarily equal to each other; and
$n$ is equal to the degree of polymerization.

14. The polymer product of claim 13 having an inherent viscosity within the range of about 0.2 to 1.0 when measured at 25° C as a 1% polymer solution in N-methyl-2-pyrrolidinone.

15. The polymer product of claim 14 containing from about 25 to 50 mole percent of bibenzyl sulfone units.

16. The polymer product of claim 13 wherein Z is oxygen and Z' is a direct link.

17. A polysulfone polymer comprising from about 1 to 99 mole percent of polymerized units having the formula:

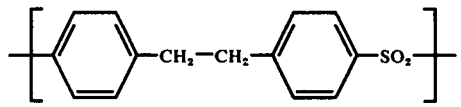

and correspondingly from about 99 to 1 mole percent of polymerized aromatic sulfone units different therefrom.

18. A shaped article prepared from the polymer of claim 17.

* * * * *